United States Patent [19]

Ono

[11] Patent Number: 4,548,505
[45] Date of Patent: Oct. 22, 1985

[54] SENSOR FOR SPECTRAL ANALYZER FOR LIVING TISSUES

[75] Inventor: Kimizo Ono, Osaka, Japan

[73] Assignee: Sumitomo Electric Industries, Ltd., Japan

[21] Appl. No.: 369,767

[22] Filed: Apr. 19, 1982

[30] Foreign Application Priority Data

Apr. 22, 1981 [JP] Japan .................................. 56-60775

[51] Int. Cl.³ .......................... G01N 21/55; A61B 5/00
[52] U.S. Cl. ...................................... 356/445; 128/634
[58] Field of Search ....................... 356/373, 375, 445; 128/6, 7, 8, 634, 4, 664, 665, 666, 667

[56] References Cited

U.S. PATENT DOCUMENTS 4,210,029  7/1980  Porter ............................. 128/634 X
4,213,462  7/1980  Sato ..................................... 128/634

FOREIGN PATENT DOCUMENTS 2140126  2/1972  Fed. Rep. of Germany ...... 356/448

Primary Examiner—Vincent P. McGraw
Attorney, Agent, or Firm—Sughrue, Mion, Zinn, Macpeak and Seas

[57] ABSTRACT

A sensor for a spectral analyzer includes a relatively movable holder and probe, where the probe is fitted with a reflector, and the holder is provided with a pair of adjacent optical fibers for transmitting/receiving light. When the probe abuts the surface of the object to be measured, the probe and holder move relatively so that the fiber pair approach the reflector. A switch activating the analyzer for data collection is operated in response to the change in reflected light intensity caused by the relative movement.

7 Claims, 6 Drawing Figures

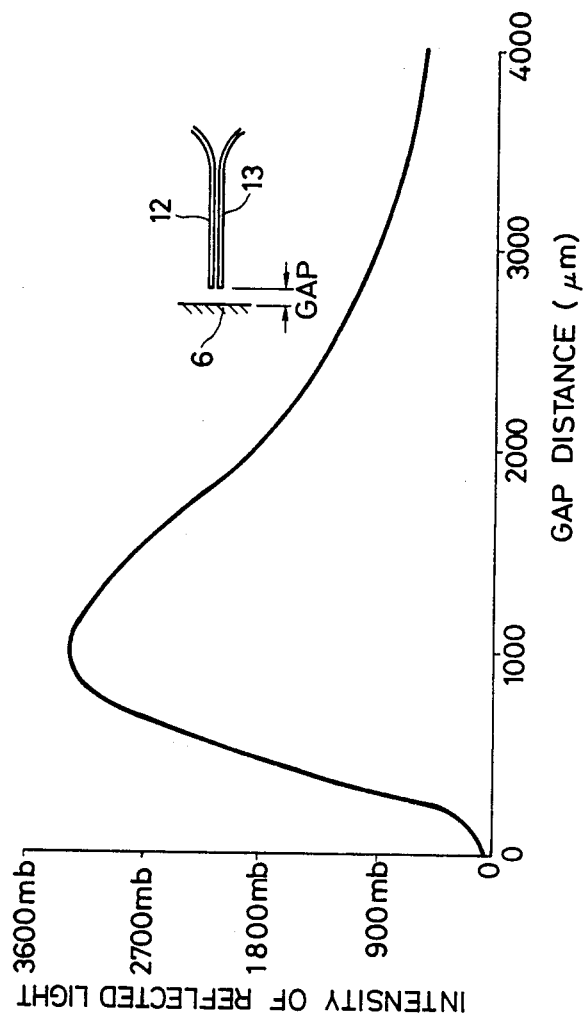

SENSOR FOR SPECTRAL ANALYZER FOR LIVING TISSUES

BACKGROUND OF THE INVENTION

The present invention relates to a sensor for use with a spectral analyzer for living tissues. The sensor is capable of obtaining data in a timely manner at constant pressure and can be handled easily with increased safety and reliability.

Spectral analysis of living tissues (the stomach, intestines, skins, tooth sockets and other parts of the living organism) is conventionally performed by one of two methods: (1) the tip of a bundle of fibers connected to the spectral analyzer is inserted into the human body either directly or with the aid of a laparoscope or a fiberscope, and while the pressure applied to the tissue is controlled with one hand, the analyzer is switched on and off with the other hand to obtain data; and (2) the tip of bundle of fibers connected to the spectral analyzer is inserted into a spring-loaded holder in the form of an elongated tube with a contact provided between the holder and fiber bundle and connected to the switching circuit in the analyzer, and the holder is inserted in the human body until the fiber bundle whose tip is being pressed against the tissue is retracted by a predetermined distance against the force of the spring, whereupon the contact is closed to start the collection of the necessary data.

In the spectral analysis of living tissues, data must be obtained as soon as the tip of the bundle of fibers contacts the tissue and before any undesired change occurs in the living tissue, and the pressure applied to the tissue by the tip of the fiber bundle is desirably held constant to maintain the local hemostatic effect. These requirements are however not fully met by either of the two conventional methods. According to the first method, there often occurs a time lag in obtaining the necessary data because it is difficult to synchronize the timing of the setting of the tip of the bundled fiber on the tissue and that of switching on the analyzer. Furthermore, this method requires both hands of the operator and is not efficient, and the pressure applied to the tissue by manual control tends to fluctuate and to lack accuracy. In the second method, a bundle of relatively heavy fibers is moved in the holder against the force of the spring, so the pressure applied to the tissue changes substantially depending upon the angle at which the holder is set on the body part.

SUMMARY OF THE INVENTION

The present invention has been accomplished to eliminate the above described defects of the conventional sensors. The invention is hereunder described by reference to the embodiments shown in the accompanying figures.

BRIEF DESCRIPTION OF THE DRAWINGS

FIG. 4 is a graph illustrating the measurement of the reflected light intensity vs. gap profile of the sensor.

DETAILED DESCRIPTION OF THE PREFERRED EMBODIMENTS

Figure 1:
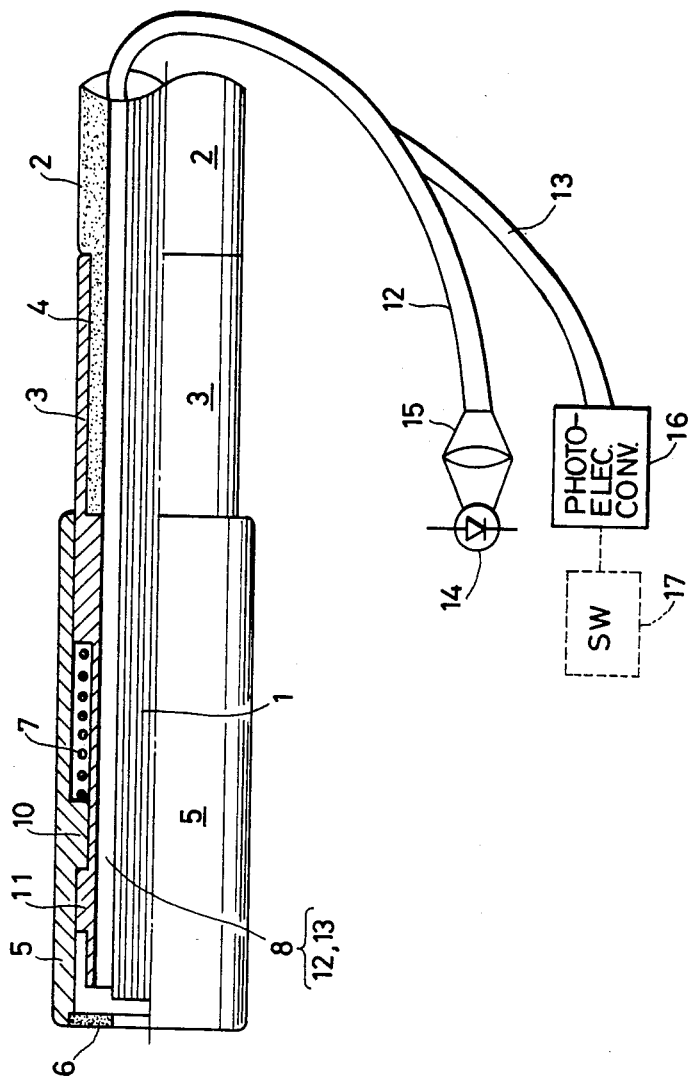
FIG. 1 is a front view, partly in section, of the essential components of the sensor of the present invention.
Figure 2:
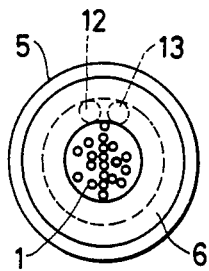
FIG. 2 is a cross section showing one end of the sensor of FIG. 1.

FIG. 1 shows the essential components of the sensor of the present invention, wherein numeral 1 indicates a bundle of fibers connected to an (unshown) spectral analyzer; 2 is a sheath or cover formed around the bundled fiber 1; 3 is a holder for holding the bundled fiber 1 in position and is connected to the tip of the sheath 2 by adhesive or other fixing means 4; 5 is a tubular probe connected to the tip of the holder 3 in an axially slidable manner; 6 is an annular reflective mirror or plate fitted in the opening in the tip of the probe 5; 7 is a spring loaded between the holder 3 and probe 5 that urges the reflector 6 away from the tip of the bundled fiber 1; and 8 is a fiber incorporated in the bundled fiber 1 for transmitting and receiving light.

As shown, the probe 5 is capable of limited axial movement relative to the holder 3, limited by means of the engagement between annular projections 10 and 11. By this arrangement, with the spring 7, the tips of the fibers 1 and 8 are held a given distance away from the reflector 6 when the sensor is not in operation. The probe 5 has a relatively small size and is made of a light material.

As shown, the fiber 8 consists of two independent fibers 12 and 13, one for transmitting light and the other for receiving light. Alternatively, the fiber may be a single fiber including a half mirror at a branch for transmitting and receiving light. As shown, the light transmitting fiber 12 is supplied with light of a given intensity from a light source 14 through a lens 15, and the light coming from the light receiving fiber 13 is converted to an electric current in a photoelectric converter 16 and compared with a reference value whereby the switch circuit 17 may be opened or closed.

Figure 3A:
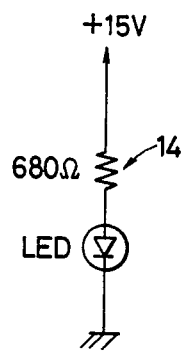
FIGS. 3(a) and 3(b) are circuit diagrams of the light source and photoelectric converter, respectively.
Figure 3B:
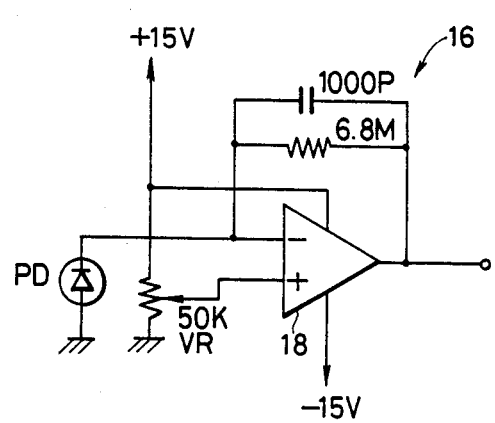

FIG. 3(a) is a circuit diagram for the light source 14 and FIG. 3(b) is a circuit diagram for the photoelectric converter 16. The light source 14 comprises a light-emitting diode (LED) which is connected to a power source through a resistor and which emits light of a given intensity which enters the light transmitting fiber 12 through the lens. The light is reflected by the annular reflector 6 and travels back through the light receiving fiber 13. Thereupon, the light is converted to an electric current by a photodiode (PD), whose output is applied to an operational amplifier 18. The operational amplifier 18 operates to convert an input current from the photodiode (PD) to a voltage signal, and the switch circuit 17 of the spectral analyzer is actuated in response to predetermined variations in the voltage signal.

The sensor of the present invention having the above described arrangement is used as follows. The holder 3 or sheath 2 is held in one hand and the probe 5 is inserted into the human body to press the outer surface of the reflector 6 against the tissue. Then, the probe 5 is retracted against the force of the spring 7, and when the distance between the reflector 6 and the tip of the bundled fiber 8 becomes smaller than a given value, the intensity of the light sent back through a feedback loop consisting of the light source 14, the light transmitting fiber 12, the reflector 6 and the light receiving fiber 13 becomes smaller than a predetermined level, to thereby close the switch circuit 17 of the spectral analyzer. A measurement of the light intensity vs. gap profile is shown in FIG. 4.

According to the sensor of the present invention, the relatively light probe 5 is supported by the spring 7 against the holder 3, so that the pressure applied to the tissue remains constant without fluctuation even if the angle at which the sensor is set on the body is varied. The necessary data can be obtained by simply pressing the sensor against the tissue with one hand, which not only improves the operability of the sensor but also achieves timely collection of data. As a further advantage, the signals for turning on and off the switch 17 are fed optically through the optical fiber 8, making the sensor safer to use yet trouble-free.

Figure 5:
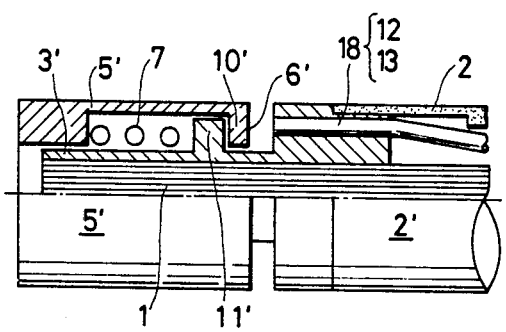
FIG. 5 shows a modification of the sensor of FIG. 1.

A modification of the sensor of the present invention is shown in FIG. 5 wherein the holder 3' and probe 5' are modified as shown, and the reflector 6' is positioned on the rear end of the probe. The light transmitting/receiving fiber 8 is positioned adjacent the bundled fiber 1 with its tip facing reflector 6'. This modified arrangement performs equally as well as the arrangement shown in FIG. 1.

What is claimed is:

1. A sensor for a spectral analyzer for living tissues comprising; a holder, a bundle of fibers held in position in said holder and connected to the analyzer, a probe including a reflector fitted to an end thereof, said probe being axially movable by a predetermined distance with respect to said holder, a light transmitting/receiving fiber connected to a switch circuit of said analyzer, and a spring positioned between said holder and said probe for urging said reflector away from a tip of the light transmitting/receiving fiber, said switch being actuated so as to be turned on in response to a decrease in the intensity of the light reflected into said fiber due to a decrease in a distance between said tip of the light transmitting/receiving fiber and said reflector.

2. The sensor as claimed in claim 1 wherein said light transmitting/receiving fiber comprises a pair of adjacent fibers adjacent said bundle of fibers.

3. The sensor as claimed in claim 1 wherein said light transmitting/receiving fiber comprises a pair of adjacent fibers incorporated in said bundle of fibers.

4. The sensor as claimed in claim 1 wherein said switch circuit comprises a photoelectric device for converting received light into a current, and amplifier means for converting said current into a voltage signal, said switch being operated in response to changes in said voltage signal.

5. The sensor as claimed in claim 1 wherein said light transmitting/receiving fiber comprises a single fiber having a branch, and a half-mirror disposed at the branch.

6. The sensor as claimed in claim 1 wherein said end of said probe fitted with said reflector faces an end of said holder.

7. The sensor as claimed in claim 1 wherein said end of said probe fitted with said reflector faces an intermediate portion of said holder containing ends of said transmitting/receiving fiber.

* * * * *